(12) United States Patent
Zhang et al.

(10) Patent No.: US 9,562,059 B2
(45) Date of Patent: Feb. 7, 2017

(54) ANTICANCER MAYTANSINOIDS WITH TWO FUSED MACROCYCLIC RINGS

(71) Applicants: Hong Kong Baptist University, Hong Kong (HK); The Board of Trustees of the University of Illinois, Urbana, IA (US)

(72) Inventors: Hongjie Zhang, Hong Kong (HK); Djaja D. Soejarto, Urbana, IL (US); Harry H. S. Fong, Urbana, IL (US)

(73) Assignees: Hong Kong Baptist University, Hong Kong (CN); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/100,985

(22) PCT Filed: Dec. 2, 2014

(86) PCT No.: PCT/CN2014/092834
§ 371 (c)(1),
(2) Date: Jun. 2, 2016

(87) PCT Pub. No.: WO2015/081857
PCT Pub. Date: Jun. 11, 2015

(65) Prior Publication Data
US 2016/0289244 A1 Oct. 6, 2016

Related U.S. Application Data

(60) Provisional application No. 61/910,718, filed on Dec. 2, 2013.

(51) Int. Cl.
*C07D 498/22* (2006.01)
(52) U.S. Cl.
CPC .................. *C07D 498/22* (2013.01)

(58) Field of Classification Search
None
See application file for complete search history.

(56) References Cited

FOREIGN PATENT DOCUMENTS

WO 2005/099754 A2 10/2005

OTHER PUBLICATIONS

Kupchan et al., Journal of the Chemical Society, Chemical Communications (1972), (19), 1065.*
Kupchan et al. (Feb. 1972), "Maytansine, a Novel Antileukemic Ansa Macrolide from Maytenus ovatus," Journal of the American Chemical Society 94(4):1354-1356.
Kupchan et al. (1978), "Structural Requirements for Antileukemic Activity among the Naturally Occurring and Semisynthetic Maytansinoids," Journal of Medicinal Chemistry 21(1):31-37.
Larson et al. (1999), "Two New Maytansinoids from Maytenus buchananii," 62(2):361-363; and Cassady et al. (2004).
"Recent Developments in the Maytansinoid Antitumor Agents," Chem. Pharm. Bull. 52(1):1-26.).
Powell et al. (1982), Journal of the American Chemical Society 104(18): 4929-34.).
[Ding Hou in Flora Malesiana I, 6 (3):399 (1964)].
Mi et al. (2002), J. Nat. Prod. 65: 842-850.
Hollingshead et al. (1995), Life Sciences 57(2):131-141.
U.S. Department of Health and Human Services, Food and Drug Administration, Center for Drug Evaluation and Research, Jul. 2005; p. 7.

* cited by examiner

*Primary Examiner* — Karl J Puttlitz
(74) *Attorney, Agent, or Firm* — Daniel R. Collopy

(57) ABSTRACT

This invention provides maytansinoids having improved tumor inhibition activity. In particular, the present invention provides a method of treatment of cancer, in particular colon cancer, using maytansinoid compounds having two fused macrocyclic rings.

14 Claims, 3 Drawing Sheets

ANTICANCER MAYTANSINOIDS WITH TWO FUSED MACROCYCLIC RINGS

CROSS-REFERENCE TO RELATED APPLICATIONS

The present application is a national phase application of the international patent application number PCT/CN2014/092834 filed on Dec. 2, 2014 which claims priority of U.S. Provisional Patent Application Ser. No. 61/910,718 filed Dec. 2, 2013 and which the disclosures are hereby incorporated by reference.

STATEMENT REGARDING FEDERALLY SPONSORED RESEARCH

This invention is made with government support under Grant 1 UO1-TW01015-01 awarded by the National Institutes of Health administered by the Fogarty International Center. The United States Government has certain rights in the invention.

FIELD OF INVENTION

This invention provides maytansinoids having improved tumor inhibition activity. In particular, the present invention provides a method of treatment of cancer, in particular colon cancer, using maytansinoid compounds having two fused macrocyclic rings.

BACKGROUND OF THE INVENTION

Maytansine is a compound found to have anticancer properties but is clinically proven to be too toxic to use in humans. Maytansine is an ansamycin antibiotic isolated from various species of the genus *Maytenus*, spiny shrubs that grow in many parts of Africa, and shows significant in vivo tumor inhibitory activity. (Kupchan et al. (February 1972), "Maytansine, a Novel Antileukemic Ansa Macrolide from *Maytenus ovates*," Journal of the American Chemical Society 94(4):1354-1356.) Maytansine is believed to bind to tubulin at the rhizoxin binding site, thereby inhibiting microtubule assembly, inducing microtubule disassembly, and disrupting mitosis. Maytansine is a highly cytotoxic natural product that fails as an anticancer agent in human clinical trials because of unacceptable systemic toxicity.

Maytansinoids are derivatives of maytansine and are potent antitumor agents found in plants and microorganisms. Maytansinoids and maytansinoid analogs with potential as anticancer drugs have been previously described in Kupchan et al. (1978), "Structural Requirements for Antileukemic Activity among the Naturally Occurring and Semisynthetic Maytansinoids," Journal of Medicinal Chemistry 21(1):31-37; and in WO 2005/099754. Existing maytansinoids mostly contain a single macrocyclic ring, although a handful of maytansinoids having two macrocyclic rings are known. (Larson et al. (1999), "Two New Maytansinoids from *Maytenus buchananii*," 62(2):361-363; and Cassady et al. (2004), "Recent Developments in the Maytansinoid Antitumor Agents," Chem. Pharm. Bull. 52(1):1-26.) Two such maytansinoids, trenudine and treflorine, which contain two fused macrocyclic rings, retain antitumor activity against KB cells and P388 lymphocytic leukemia. (Powell et al. (1982), Journal of the American Chemical Society 104(18): 4929-34.)

It is a goal of the present invention to provide new maytansinoid compounds having improved antitumor activity and/or having reduced systemic toxicity in humans for cancer treatment.

SUMMARY OF THE INVENTION

The objective of the present invention is to provide maytansinoid compounds having antitumor activity. Compounds of the present invention have improved antitumor activity and/or reduced toxicity compared to maytansine and known maytansinoids.

The present invention provides maytansinoid compounds having two fused macrocyclic rings in the structure instead of one macrocyclic ring. Known maytansinoids and maytansinoid analogues have one macrocyclic ring. The presence of an additional macrocylic ring in the maytansinoids of the present invention leads to more beneficial anticancer effect from that of other maytansine derivatives.

*Loeseneriella pauciflora* is a plant belonging to the Celastraceae family (or staff vine or bittersweet family; syn. Canotiaceae, Chingithamnaceae, Euonymaceae, Goupiaceae, Lophopyxidaceae, and Siphonodontaceae in Cronquist system), a family of about 90-100 genera and 1,300 species of vines, shrubs and small trees, belonging to the order Celastrales. The great majority of the genera are tropical, with only *Celastrus* (the staff vines) and *Euonymus* (the spindles) widespread in temperate climates. Another embodiment of the present invention provides a composition comprising one or more maytansinoid compounds.

The compounds of the present invention show improved tumor inhibition activity against KB, Col-2, LNCaP, Lu-1, and MCF-7 cancer cells than maytansine.

In a first aspect of the present invention, there is provided a compound having the structure of:

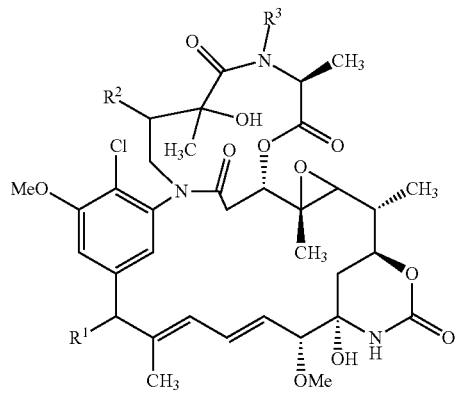

Formula I wherein $R^1$, $R^2$, and $R^3$ are independently selected from the group consisting of hydrogen and an alkyl group having between 1 and 6 carbon atoms.

In a first embodiment of the first aspect of the present invention, a compound having a structure of Formula I is provided, wherein $R^1$ is hydrogen, $R^2$ is a methyl group, and $R^3$ is hydrogen.

In a second embodiment of the first aspect of the present invention there is provided a compound having the structure of:

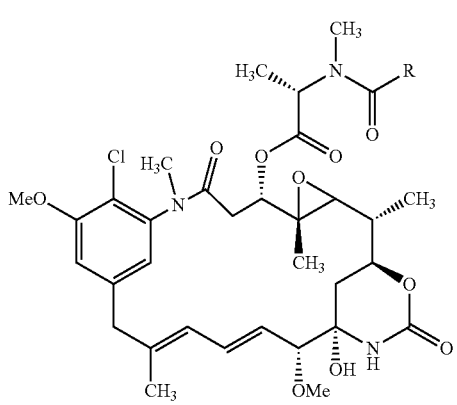

Formula II wherein R is a substituted or non-substituted chain alkyl group having at least 3 carbon atoms and no more than 8 carbon atoms.

In one example of the second embodiment of the first aspect of the present invention, a compound having a structure of Formula II is provided, wherein R is $CH_2CH_2CH_3$.

In the third embodiment of the first aspect of the present invention, there is provided a compound having the structure:

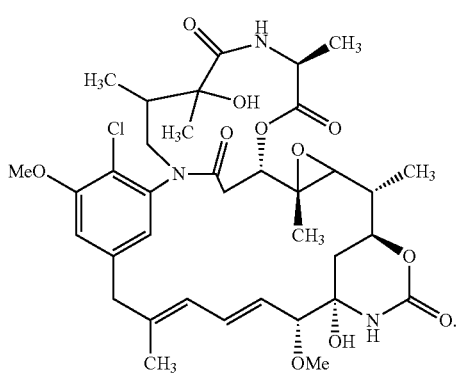

Formula III

In a forth embodiment of the first aspect of the present invention, there is provided an extract from the plant *Loeseneriella pauciflora* having one or more maytansinoid compounds, wherein said extract exhibits antitumor activity.

In a second aspect of the present invention, there is provided a method of treating cancer, comprising: administering an effective dose of at least one compound according to any one of example or embodiment of the present invention daily.

In a first embodiment of the second aspect of the present invention, the effective dosage is about 20 µg/kg per patient body weight, preferably about 40 µg/kg per patient body weight, or preferably about 0.05 mg/kg per patient body weight.

In a second embodiment of the second aspect of the present invention, the effective dosage is at least 1.6 µg/kg per patient body weight, preferably about 3.2 µg/kg per patient body weight or preferably about 0.004 mg/kg per patient body weight.

In a third embodiment of the second aspect of the present invention, the cancer treated is colon carcinoma, oral epidermoid carcinoma, promyelocytic leukemia, prostate carcinoma, breast carcinoma, or lung carcinoma.

BRIEF DESCRIPTION OF DRAWINGS

The above and other objects and features of the present invention will become apparent from the following description of the invention, when taken in conjunction with the accompanying drawings, in which.

DETAILED DESCRIPTION OF THE INVENTION

Figure 1:
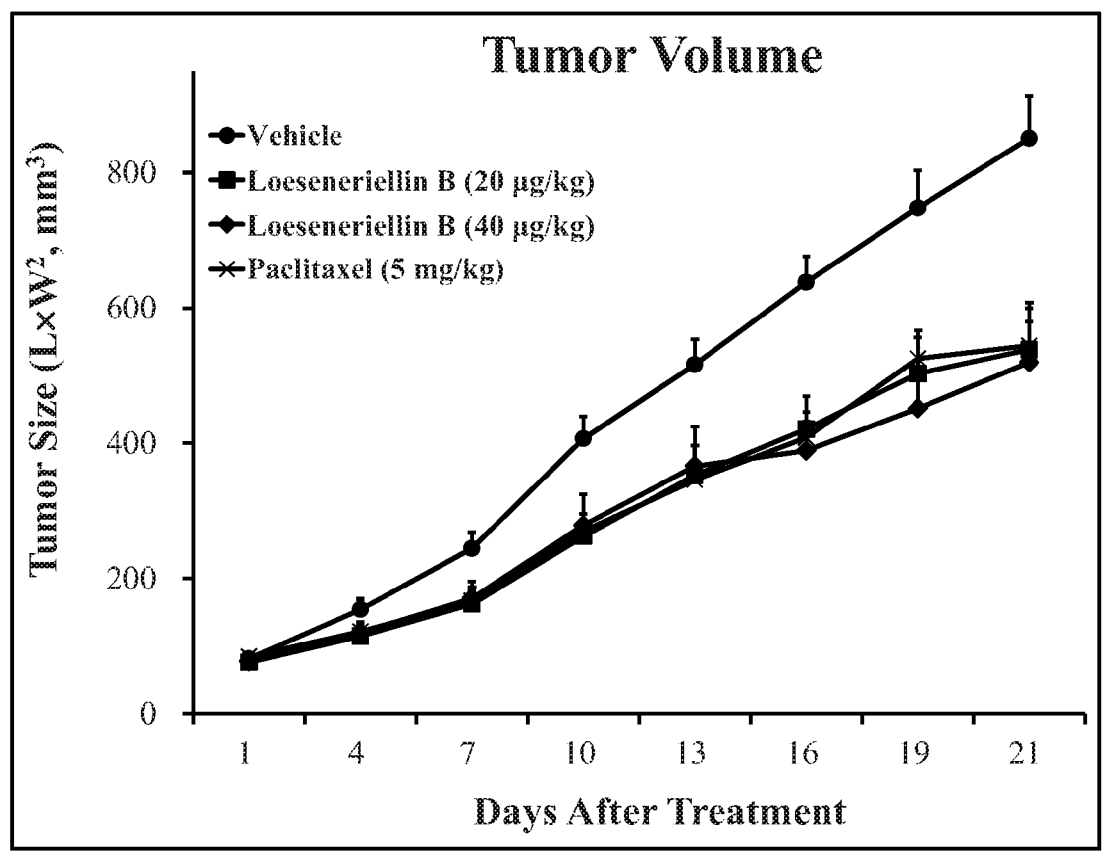
FIG. 1 shows the tumor growth curve of HCT116-tumor xenograft after three weeks of treatment with Paclitaxel and loeseneriellin B.

Bioassay directed-fractionation of the stem barks of *Loeseneriella pauciflora* (DC.) A.C. Sm (Celastraceae) lead to isolation of new maytansinoid compounds of the present invention. "Bioassay-directed fractionation" is the sequential reduction of complex mixtures eventually to individual components. The extracts are tested for biological effects and subjected to one or several fractionation procedures. After each separation step the fractions are biotested for selection of active fractions for further investigation. When the complexity of the mixture is reduced to a few individual compounds, the fractions will be purified to obtain bioactive compounds, which are subjected to chemical identification and further bioactivity evaluation.

The present invention provides a compound having a structure of

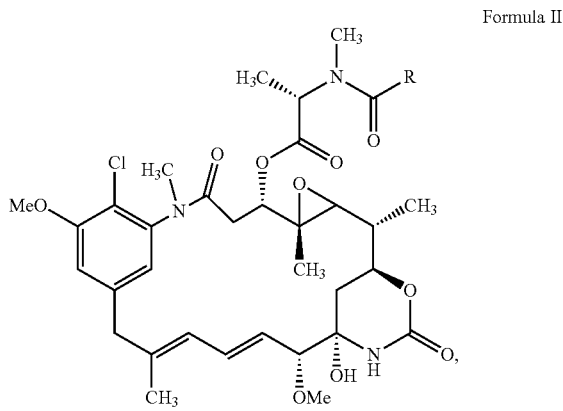

Formula II wherein R is a straight chain alkyl group having at least 3 carbon atoms. The alkyl group is optionally substituted by one or more of an alcohol, an amino alcohol, an amine, an amide, or an ether. In one embodiment, the present invention provides a compound of Formula II, Loeseneriellin A, wherein R is $CH_2CH_2CH_3$. The structures of Loeseneriellin A, maytansine and other common maytansinoids are as follows:

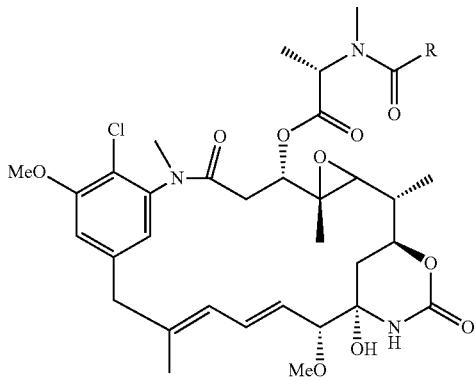

Maytansine: R = CH₃
Maytanprine: R = CH₂CH₃
Maytanbutine: R = CH(CH₃)₂
Maytanvaline: R = CH₂CH(CH₃)₂
Loeseneriellin A: R = CH₂CH₂CH₃

The maytansinoid compounds of the present invention have two fused macrocyclic rings, which are rarely found in nature. A compound having a "macrocyclic ring" is an organic compound that contains a large ring. In the organic chemistry of alicyclic compounds, a closed chain of approximately 12 atoms is usually regarded as the minimum size for a large ring; crown ethers are similarly defined. Macrocyclic compounds may be a single, continuous thread of atoms, such as cyclododecane [(CH₂)₁₂], or may include more than one strand or other ring systems (subcyclic units) within the macrocycle or macroring. In addition, macrocycles may be composed of aromatic rings that confer considerable rigidity upon the cyclic system.

Since the discovery of maytansine from *Maytenus ovatus* in 1972 as a potent cytotoxic agent, 53 more maytansinoids have been identified from nature including plants, microorganisms and mosses. However, only four maytansinoid structures are reported to contain two fused macrocyclic rings. The present invention also provides a compound of Formula III, Loeseneriellin B, comprises a fused bimacrocyclic rings. A major structural difference of Loeseneriellin B to the four existing compounds having two macrocyclic rings shown below (maytanbicyclinol, treflorine, N-methyltrenudone, trenudine) is that Loeseneriellin B formed a carbon-carbon bond between a methyl group and C-5'.

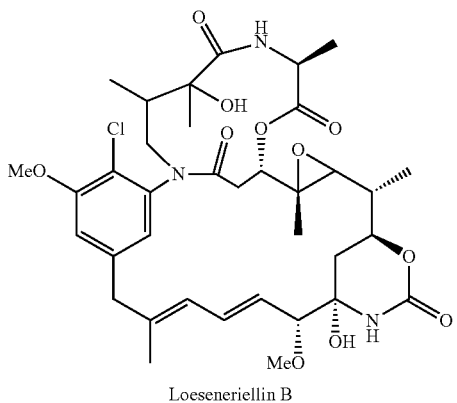

Loeseneriellin B

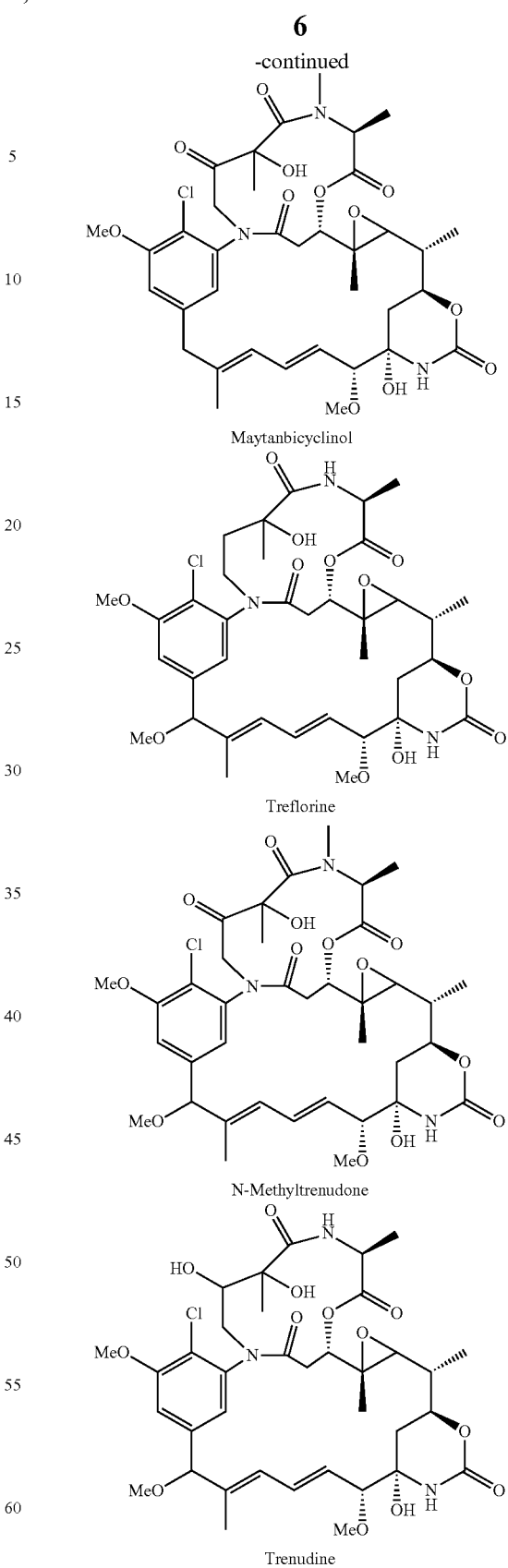

Maytanbicyclinol

Treflorine

N-Methyltrenudone

Trenudine

In first embodiment of the first aspect of the present invention, the present invention provides a compound having the structure:

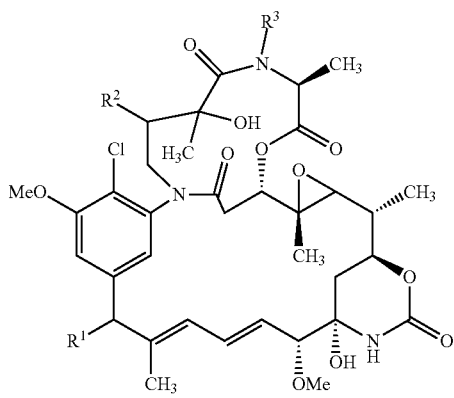

Formula I wherein $R^1$, $R^2$, and $R^3$ are independently selected from the group consisting of hydrogen and an alkyl group having between 1 and 6 carbon atoms.

In one embodiment, the present invention provides a compound of Formula I, wherein $R^1$ is hydrogen, $R^2$ is a methyl group, and $R^3$ is hydrogen.

In a second embodiment of the first aspect of the present invention there is provided a compound having the formula:

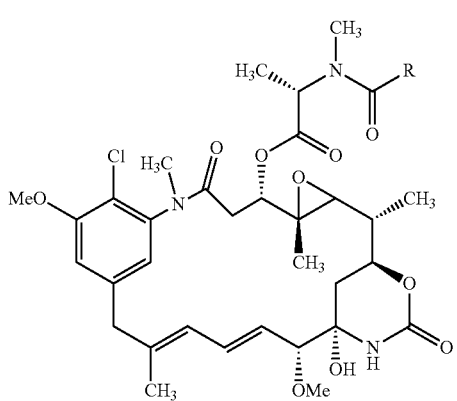

Formula II wherein R is a substituted or non-substituted alkyl group having at least 3 carbon atoms and no more than 8 carbon atoms.

In one example of the second embodiment of the first aspect of the present invention, the present invention provides a compound of Formula II, wherein R is $CH_2CH_2CH_3$.

In the third embodiment of the first aspect of the present invention there is provided a compound having the structure:

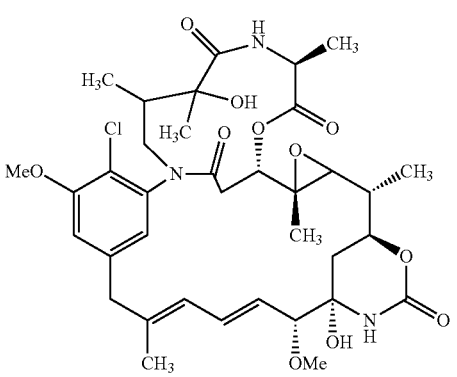

Formula III

In a forth embodiment of the first aspect of the present invention there is provided an extract from the plant *Loeseneriella pauciflora* having one or more maytansinoid compounds, wherein said extract exhibits antitumor activity.

In a second aspect of the present invention, there is provided a method of treating cancer, comprising: administering an effective dose of at least one compound according to any one of example or embodiment of the present invention daily.

In a first embodiment of the second aspect of the present invention, the effective dosage is about 20 μg/kg per patient body weight, preferably about 40 μg/kg per patient body weight, or preferably about 0.05 mg/kg per patient body weight.

In a second embodiment of the second aspect of the present invention, the effective dosage is at least 1.6 μg/kg per patient body weight, preferably about 3.2 μg/kg per patient body weight or preferably about 0.004 mg/kg per patient body weight.

In a third embodiment of the second aspect of the present invention, the cancer treated is colon carcinoma, oral epidermoid carcinoma, promyelocytic leukemia, prostate carcinoma, breast carcinoma, or lung carcinoma.

EXAMPLES

Example 1

Activity of Maytansinoid Compounds in Cell Culture

*Loeseneriella pauciflora* (DC.) A.C. Sm (Celastraceae) is collected from Cue Phuong National Park (Nho Quan District, Ninh Binh Province, Vietnam) as part of an International Cooperative Biodiversity Group (ICBG) project, which addresses the related issues of biodiversity conservation, economic growth, and promotion of health through the discovery of anticancer, anti-human immunodeficiency virus (anti-HIV), anti-malarial and anti-tubercular (anti-TB) natural products through collaboration with institutions in Vietnam, Laos and USA. Chloroform extract of *L. pauciflora* exhibits potent inhibition activities against KB, Col-2, LNCaP, LU-1, HUVEC cells with $IC_{50}$ values of less than 0.16 μg/ml during initial bioassay. A 5.9 kg sample of dried stem barks of this plant is thus re-collected from the Vietnamese National Park in order to identify anticancer compounds. As a result, two new (1-2) and four known maytansinoids (3-6) are isolated from this plant by bioassay-guided fractionation studies.

The recollected stembark (5.9 kg) of *L. pauciflora* is extracted with MeOH to afford an extract (360 g). Bioassy-guided fractionation of the MeOH extract by column chromatography on Si gel and RP-18 Si gel and subsequent preparative HPLC separation led to the isolation of two new maytansinoids, loeseneriellin B (1) and loeseneriellin A (2), together with other four known maytansinoids: maytansine (3), maytanprine (4), maytanbutine (5) and maytanvaline (6).

Loeseneriellin B (1) is obtained as a white powder with a molecular formula of $C_{36}H_{48}ClN_3O_{11}$ by positive HRESIMS ([M+H]$^+$ m/z 734.30282, calcd. 734.30556) and NMR studies. The compound is rapidly elucidated to be a maytansinoid by comparison of its $^1$H and $^{13}$C NMR data to those of maytansine compounds. Differences, especially for H-3, H-17 and the proton signals on the side chain, are observed between the $^1$H NMR spectrum of 1 and those of the usual maytansinoids. Analysis of 2D NMR data including $^1$H-$^1$H COSY, HMQC, HMBC and ROESY spectra revealed that the side chain in 1 formed a new ring by connecting to the nitrogen atom of C-18. The structure of loeseneriellin B is thus determined as 1 (Formula III).

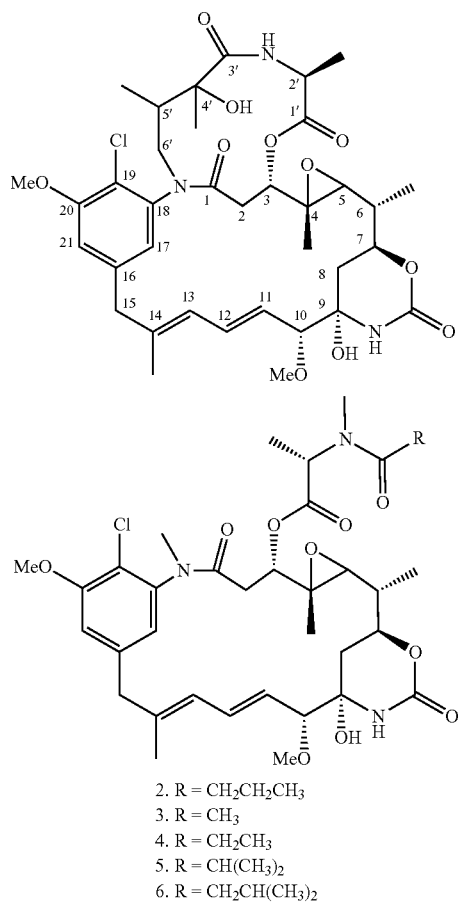

2. R = CH$_2$CH$_2$CH$_3$
3. R = CH$_3$
4. R = CH$_2$CH$_3$
5. R = CH(CH$_3$)$_2$
6. R = CH$_2$CH(CH$_3$)$_2$

The in vitro anti-tumor activity of isolated compounds (1-6) is evaluated against KB, Col-2, LNCaP, Lu-1, and MCF-7 cell lines. All of the compounds exhibit extremely high cytotoxic activity with IC$_{50}$ values of less than 0.6 ng/mL against tumor cell lines. The new bimacrocyclic compound, loeseneriellin B (1), shows comparable bioactivity to that of maytansine (3). However, because of the much different stereochemistry, the bimacrocyclic maytansinoid may have a different anticancer therapeutic window from that of mono-macrocyclic maytansine derivatives.

TABLE 1

Anti-tumor activity of compounds 1-6 in tumor cell culture[a]

| Compound | KB | Lu1 | Col2 | LNCaP | MCF-7 |
| --- | --- | --- | --- | --- | --- |
| 1 Loeseneriellin B | 0.15 | 0.71 | 0.20 | 0.25 | 0.68 |
| 2 Loeseneriellin A | 0.10 | 0.38 | 0.18 | 0.18 | 0.19 |
| 3 Maytansine | 0.17 | 0.77 | 0.19 | 0.32 | 0.69 |
| 4 Maytanprine | 0.061 | 0.35 | 0.16 | 0.16 | 0.17 |

TABLE 1-continued

Anti-tumor activity of compounds 1-6 in tumor cell culture[a]

| Compound | KB | Lu1 | Col2 | LNCaP | MCF-7 |
| --- | --- | --- | --- | --- | --- |
| 5 Maytanbutine | 0.050 | 0.13 | 0.061 | 0.054 | 0.13 |
| 6 Maytanvaline | 0.11 | 0.69 | 0.15 | 0.16 | 0.27 |

[a]Results are expressed as IC$_{50}$ values in nM [concentration required to inhibit cell growth by 50%], and data were obtained from triplicate experiments. Vinblastine and paclitaxel are used as a positive control (vinblastine showed 91%, 54%, 87%, 89% and 70% inhibition against KB, Lu-1, Col2, LNCaP and MCF-7 at 40 ng/mL, respectively; paclitaxel showed 93%, 56%, 76%, 89% and 71% inhibition against KB, Lu-1, Col2, LNCaP and MCF-7 at 20 ng/mL, respectively.)

General Experimental Procedures.

Optical rotations are measured on a Perkin-Elmer model 241 polarimeter. IR spectra are run on a Jasco FT/IR-410 spectrometer, equipped with a Specac Silver Gate ATR system by applying a film on a Germanium plate, 1D and 2D NMR spectra are recorded on a Bruker Avance-500 MHz spectrometer. Column chromatography is carried out on silica gel (200-400 mesh, Natland International Corporation), and reversed-phase flash chromatography is accomplished with RP-18 silica gel (40-63μ, EM Science). Reversed-phase HPLC is carried out on a Waters 600E Delivery System pump, equipped with a Waters 996 photodiode detector, and a Phenomenex LUNA C18 column (10μ, 250×50 mm), which also result in extracting UV spectral data of each purified compound. Thin-layer chromatography is performed on Whatman glass-backed plates coated with 0.25 mm layers of Silica gel 60. HRTOFMS spectra are recorded on a ThermoFinnigan LTQFT spectrometer.

Plant Material.

The initial collection of stem bark sample (SV-2194) of Loeseneriella pauciflora (DC.) A.C. Sm (Celastraceae) is made on Aug. 15, 2000 in Cuc Phuong National Park, in a secondary valley forest 1 km distance from Bong/Park Center, with coordinate readings of 105° 43.10' N and 20° 14.60' E, at an altitude of 200 m. Voucher specimens N.M. Cuong, D.T. Kien and M.V. Sinh #975 are collected and are in deposit at the Herbarium of Cue Phuong National Park and at the Herbarium of the Field Museum, Chicago (Accession #2228062). A larger amount of the plant sample for the current isolation work, consisting of the same plant part (stem bark); sample SVA2194, 5.9 kg, is subsequently re-collected from plants located in the same area. Voucher specimens N.M. Cuong #1653 is in deposit at the Herbarium of Cue Phuong National Park, Vietnam.

Taxonomic Identification.

Taxonomic identification of the source material (NMC et al. 975 and NMC et al. 1653) is performed through comparison with identified herbarium specimens of Loeseneriella pauciflora (DC.) A.C. Sm., in deposit at the Herbarium of the Field Museum, as well as with the literature reference [Ding Hou in Flora Malesiana I, 6 (3):399 (1964)].

Cell Cultures.

Human oral epidermoid carcinoma KB cell line, human promyelocytic leukemia HL-60 cell line, human prostate carcinoma LNCaP cell line, human breast carcinoma MCF-7 cell line, human colon carcinoma Col2 cell line, and human lung carcinoma Lu1 cell line are activated from the frozen cells that are stored in Department of Medicinal Chemistry and Pharmacognosy, University of Illinois at Chicago, Chicago, Ill. Col2 cells are maintained in MEME medium. KB cells are maintained in DMEM medium. LNCaP cells are maintained in RPMI1640 medium with hormone-free 10% heat-activated FBS (fetal bovine serum) supplemented with 0.1 nM testosterone, Lu1 cells are cultured in MEME medium. MCF-7 cells are maintained in MEME medium containing 10 mg/L of insulin. In each case, PSF (100 units/mL penicillin G, 100 μg/mL streptomycin sulfate, 250 ng/mL amphotericin B) is added. All media are supplemented with 10% heat-inactivated FBS.

Cell Culture Panel Bioassays.

Extracts, fractions, and compounds are tested in a human oral epidermoid carcinoma (KB) cell line using established protocols. In addition, all pure compounds are evaluated against the other human cancer cell lines comprising our cytotoxicity screening panel. Cytotoxicity assays involving colon (Col-2), prostate (LNCaP), and lung (Lu1) carcinoma cell lines are performed using sulforhodamine B according to established protocols.

Example 2

Activity of Maytansinoid Compounds in Hollow Fiber Tests

Hollow fiber tests are well known in the art for providing preliminary indications of therapeutic efficacy (Mi et al. (2002), J. Nat. Prod. 65: 842-850). In hollow fiber tests, human tumor cell lines currently employed in cell cultures are grown inside semipermeable hollow fibers to form heterogeneous solid tumor models. The hollow fibers containing the human tumor cells are implanted in the intraperitoneal or subcutaneous compartments of host mice, and the mice treated with the test compound of interest (Hollingshead et al, (1995), Life Sciences 57(2):131-141). By evaluating the test compound's inhibition of tumor cell growth versus the toxic response in the host, a preliminary estimate of therapeutic efficacy is provided in a cost- and time effective manner.

Loeseneriellin B isolated from *Loeseneriella pauciflora* (Celastraceae) is tested for in vivo hollow fiber study. For comparison, similar in vivo hollow fiber studies are conducted using Paclitaxel (Taxol). The hollow fiber experiments reveal that loeseneriellin B is able to inhibit growth of Col2 and MCF7 cells implanted at the i.p. compartments more than 65% with a dose as low as 0.05 mg/kg (Table 2). The in vivo hollow fiber data demonstrate clearly the anticancer potency of this compound.

TABLE 2

Hollow fiber in vivo data of loeseneriellin B

| Compound | Tumor Cells | Dose (mg/kg) | Inhibition (%) | P value |
|---|---|---|---|---|
| Loeseneriellin B | Lu1-IP | 0.05 | 34.9 | 0.09 |
| | Lu1-SC | 0.05 | 0 | |
| | Lu1-IP | 0.1 | 20.9 | 0.24 |
| | Lu1-SC | 0.1 | 0 | |
| | Col2-IP | 0.05 | 65.5 | 0.009 |
| | Col2-SC | 0.05 | 0 | |
| | Col2-IP | 0.1 | 70.5 | 0.008 |
| | Col2-SC | 0.1 | 1.4 | |
| | MCF7-IP | 0.05 | 57.2 | 0.058 |
| | MCF7-SC | 0.05 | 0 | |
| | MCF7-IP | 0.1 | 75.5 | 0.008 |
| | MCF7-SC | 0.1 | 0 | |
| | MCF7-IP | 0.2 | 84.6 | 0.007 |
| | MCF7-SC | 0.2 | 40.1 | 0.25 |
| Paclitaxel (Taxol) | Lu1-IP | 2.0 | 39.9 | 0.052 |
| | Lu1-SC | 2.0 | 0 | |
| | Col2-IP | 2.0 | 62.9 | 0.006 |
| | Col2-SC | 2.0 | 6.9 | |
| | MCF7-IP | 2.0 | 71.3 | 0.007 |
| | MCF7-SC | 2.0 | 0 | |

In the conversion calculation from the tested animal doses to human clinical doses is based on the Guidance for Industry Estimating the Maximum Safe Starting Dose in Initial Clinical Trials for Therapeutics in Adult Healthy Volunteers, which was published by U.S. Department of Health and Human Services, Food and Drug Administration, Center for Drug Evaluation and Research, July 2005; Page 7: Table 1:

Human equivalent dosage (mg/kg)=animal dosage (mg/kg)×(animal Km/human Km), wherein mouse Km is 3 and human Km is 37.

Thus, 0.05 mg/kg per mouse body weight corresponds to 0.004 mg/kg per patient body weight in humans.

Example 3

Activity of Maytansinoid Compounds in HCT116 Xenograft Mouse Model

To further assess the anticancer activity of the maytansinoid compounds loeseneriellin B, loeseneriellin B is tested for its antitumor activity against HCT116 cancer cells using a number of nude mice (Balc/nu/nu, male, 5-6 weeks old, purchased from Charles River Laboratories) in comparison of paclitaxel. HCT116 cancer cells ($2 \times 10^7$ cells in 100 μL suspension) are subcutaneously implanted in the rear flank of each mouse. After 10 days, solid tumors appear at the implanted sites. The mice are then divided into four groups: one high dose (40 μg/kg: 7 mice) and one low dose (20 μg/kg: 7 mice) groups of loeseneriellin B, one dose (5 mg/kg: 10 mice) of paclitaxel and one dose of vehicle (negative control: 10 mice). Daily injections at i.v. sites were scheduled for 21 days.

In the conversion calculation from the tested animal doses to human clinical doses is based on the Guidance for Industry Estimating the Maximum Safe Starting Dose in initial Clinical Trials for Therapeutics in Adult Healthy Volunteers, which is published by U.S. Department of Health and Human Services, Food and Drug Administration, Center for Drug Evaluation and Research, July 2005; Page 7: Table 1, 20 μg/kg per mouse body weight corresponds to 1.6 μg/kg per patient body weight in humans. Correspondingly, 40 μg/kg per mouse body weight corresponds to 3.2 μg/kg per patient body weight in humans.

Figure 2:
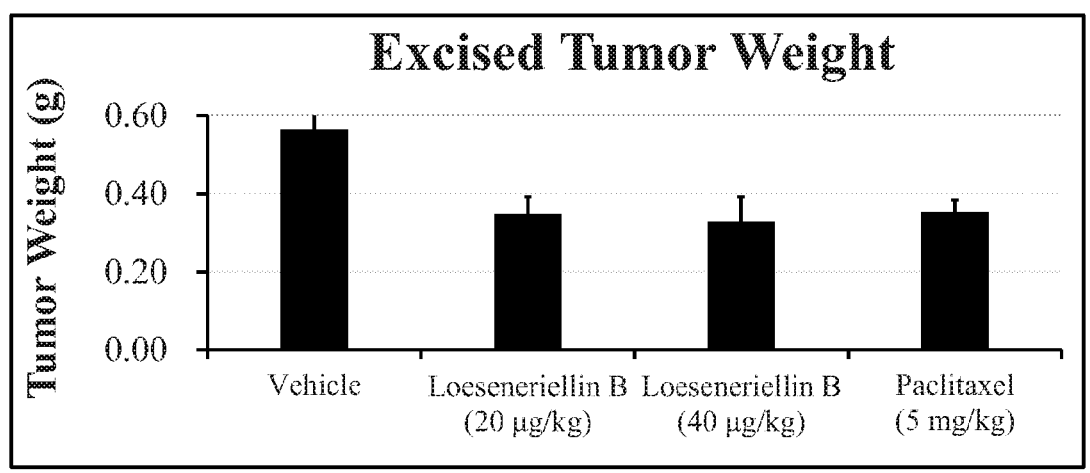
FIG. 2 shows the excised tumor weights after three weeks of treatment with Paclitaxel and loeseneriellin B.
Figure 3:
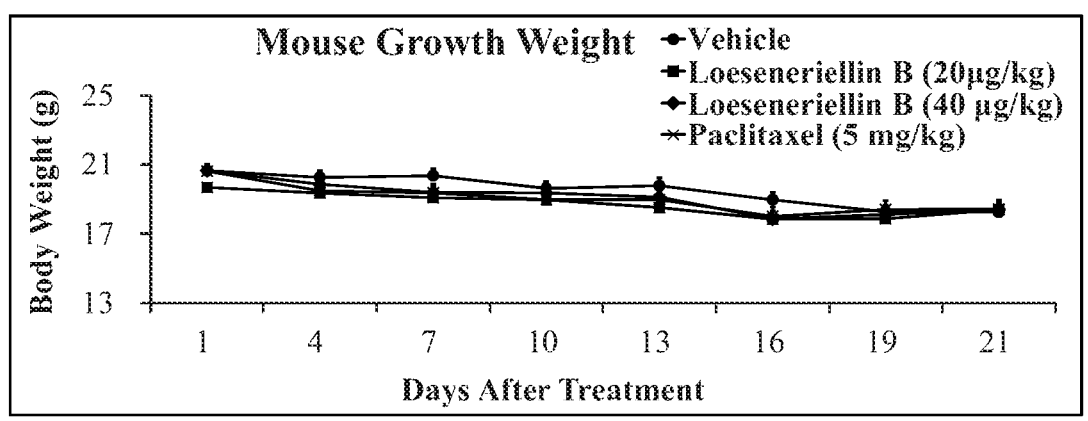
FIG. 3 shows the body weights of mice having HCT116-tumor xenograft after three weeks treatment with Paclitaxel and loeseneriellin B.

In the experiment, it is observed that HCT116 tumors in mice treated with loeseneriellin B grow slower than those in mice treated with vehicle (FIGS. 1-3). After 21 days' administration, the measured average tumor size (L×W×W) is suppressed by 38.3% with treatment of low dose of loeseneriellin B (p value=0.002) and 41.7% with treatment of high dose of loeseneriellin B (p value=0.003) in comparison with the control group. Loeseneriellin B shows similar tumor suppression to that of paclitaxel at much lower doses. No apparent weight loss for loeseneriellin B groups is observed at the two doses.

FIGS. 1 to 3 show the inhibition of HCT116-tumor xenograft growth by loeseneriellin B. The treatment started on the $10^{th}$ day when the tumor size reached approximately 100 mm³ (L×W×W). Two doses of loeseneriellin B (20 and 40 μg/kg), paclitaxel (5 mg/kg) and vehicle are administered (i.v.), respectively, to the tumor-bearing mice daily for 3 weeks (FIG. 1). FIG. 2 shows the excised tumor weights after 3 weeks of treatment; P versus control (% inhibition): loeseneriellin B high dose=0.003 (41.7%), loeseneriellin B low dose=0.002 (38.3%), and paclitaxel=0.0004 (37.6%); and FIG. 3 shows the body growth weights of mice. FIG. 3 shows body weights of mice having HCT116-tumor xenograft growth after 3 weeks of treatment. It is shown that insignificant change in body weights after treatment with positive control (Paclitaxel), loeseneriellin B or no treatment.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

As used herein, "comprising." is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A method of treating cancer, comprising: administering daily a composition comprising an effective dose of at least one compound selected from the group consisting of

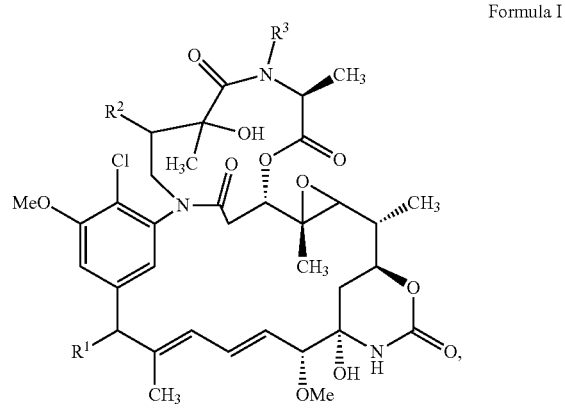

Formula I wherein $R^1$, $R^2$, and $R^3$ are independently selected from the group consisting of hydrogen and an alkyl group having 1 to 6 carbon atoms, and

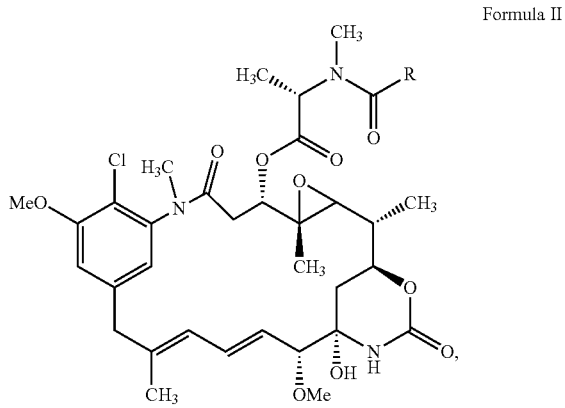

Formula II wherein R is $CH_2CH_2CH_3$.

2. The method according to claim 1, wherein the effective dosage is at least 1.6 µg/kg per patient body weight.

3. The method according to claim 1, wherein the effective dosage is about 3.2 µg/kg per patient body weight.

4. The method according to claim 1, wherein the effective dosage is about 0.004 mg/kg per patient body weight.

5. The method according to claim 1, wherein the effective dosage is about 20 μg/kg per patient body weight.

6. The method according to claim 1, wherein the effective dosage is about 40 μg/kg per patient body weight.

7. The method according to claim 1, wherein the effective dosage is about 0.05 mg/kg per patient body weight.

8. The method according to claim 1, wherein the cancer treated is colon carcinoma.

9. The method according to claim 1, wherein the cancer treated is oral epidermoid carcinoma.

10. The method according to claim 1, wherein the cancer treated is promyelocytic leukemia.

11. The method according to claim 1, wherein the cancer treated is prostate carcinoma.

12. The method according to claim 1, wherein the cancer treated is breast carcinoma.

13. The method according to claim 1, wherein the cancer treated is lung carcinoma.

14. The method according to claim 1, wherein the compound is a compound of Formula III:

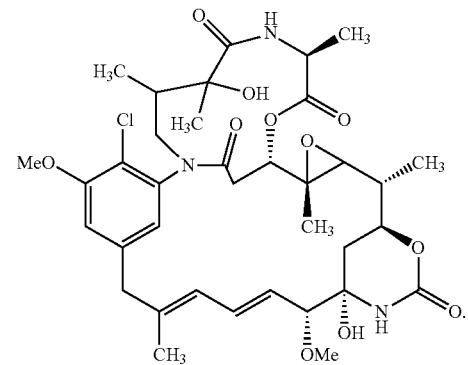

Formula III

* * * * *